US009834448B2

(12) United States Patent
Ramachandran et al.

(10) Patent No.: US 9,834,448 B2
(45) Date of Patent: Dec. 5, 2017

(54) PREPARATION OF AMINE-BORANES, INCLUDING AMMONIA BORANE (71) Applicant: PURDUE RESEARCH FOUNDATION, West Lafayette, IN (US)

(72) Inventors: P Veeraraghavan Ramachandran, West Lafayette, IN (US); Ameya Sanjay Kulkarni, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 217 days.

(21) Appl. No.: 14/879,844

(22) Filed: Oct. 9, 2015

(65) Prior Publication Data
US 2016/0101984 A1   Apr. 14, 2016

Related U.S. Application Data (60) Provisional application No. 62/061,842, filed on Oct. 9, 2014.

(51) Int. Cl.
C01B 35/14       (2006.01)
C07F 5/02        (2006.01)

(52) U.S. Cl.
CPC ............ *C01B 35/146* (2013.01); *C07F 5/027* (2013.01)

(58) Field of Classification Search
None
See application file for complete search history.

(56) References Cited

U.S. PATENT DOCUMENTS

| | | | | |
|---|---|---|---|---|
| 2004/0147781 A1* | 7/2004 | Huang | ............... | C07F 5/022 564/9 |
| 2009/0274613 A1* | 11/2009 | Hamilton | ............... | C01B 3/04 423/648.1 |
| 2009/0278085 A1* | 11/2009 | Burkhardt | ............... | C07C 29/143 252/182.29 |
| 2009/0291039 A1* | 11/2009 | Autrey | ............... | C01B 3/001 423/285 |
| 2010/0272623 A1* | 10/2010 | Lukacs, III | ............... | C01B 35/14 423/285 |
| 2013/0225863 A1* | 8/2013 | Ramachandran | ............... | C01B 35/14 564/9 |

OTHER PUBLICATIONS

Cowley A.H. et al. A Study of the Donor-Acceptor Bond in Phosphine-Borane Complexes. Journal of the American Chemical Society, 1971, 93, 6815-6821.

Brown, H.C., Studies in Stereochemistry. V. The Effect of F-Strain on the Relative Base Strengths of Ammonia and Trimethylamine. Journal of the American Chemical Society, 1993, vol. 14 No. 1, 374-378.

Ramchandran, P. et al., One-Pot Synthesis of Ammonia-Borane and Trialkylamine-Boranes from Trimethyl Borate. Organic Lett. 14 (2012) 6119-6121.

(Continued)

*Primary Examiner* — Wayne Langel
(74) *Attorney, Agent, or Firm* — Purdue Research Foundation (57) ABSTRACT Disclosed herein is a method for preparing amine-boranes.

4 Claims, 1 Drawing Sheet (56) References Cited

OTHER PUBLICATIONS

Ramchandran, P. et al., Preparation of Ammonia Borane in High Yield and Purity, Methanolysis, and Regeneration. Inorg. Chem. 2007, 46, 7810-7817.
Shaw, W. J., et al., In Situ Multinuclear NMR Spectroscopic Studies of the Thermal Decomposition of Ammonia Borane in Solution. Angew. Chem. Int. Ed. 2008, 47, 7493-7496.
Potter, R.G., et al., Thermochemistry of Lewis Adducts of BH3 and Nucleophilic Substitution of Triethylamine on NH3BH3 in Tetrahydrofuran. Inorg. Chem. 2010, 49, 10512-10521.
Muller, K., et al., Amine Borane Based Hydrogen Carriers: An Evaluation. Energy Fuels 2012, 26, 3691-3696.
Ramachandran, P., et al., Reductive Amination Using Ammonia Borane. Tetrahedron Letters 51 (2010) 3167-3169.
Sonnenschein, M.F., et al., Poly(acrylateiepoxy) Hybrid Adhesives for Low-Surface-Energy Plastic Adhesion. Journal of Polymer Science: Part A: Polymer Chemistry, vol. 45, 989-998 (2007).
Burkhardt, E.R., et al., Boron Reagents in Process Chemistry: Excellent Tools for Selective Reductions. Chem. Rev. 2006, 106, 2617-2650.

\* cited by examiner

FIG. 1

PREPARATION OF AMINE-BORANES, INCLUDING AMMONIA BORANE

CROSS-REFERENCE TO RELATED APPLICATIONS

The present patent application is related to and claims the priority benefit of U.S. Provisional Patent Application Ser. No. 62/061,842, filed Oct. 9, 2014, the contents of which is hereby incorporated by reference in its entirety into this disclosure.

TECHNICAL FIELD

The present disclosure relates to the preparation of amine-boranes, including ammonia borane.

BACKGROUND

This section introduces aspects that may help facilitate a better understanding of the disclosure. Accordingly, these statements are to be read in this light and are not to be understood as admissions about what is or is not prior art.

Amine- and phosphine-boranes,[1,2] the classic Lewis base-Lewis acid (LB-LA) pairs are known for over a century.[3] During the initial days, their methods of preparation and properties were the primary focus of chemists.[4] Amine-boranes can be readily prepared via ligand exchange using borane-tetrahydrofuran (borane-THF) or borane-methyl sulfide (BMS).[1a,5] The low molarity of the former, the stench of the latter and the pyrophoric nature of both are some of the major drawbacks associated with these procedures. In addition, removal of dimethyl sulfide for re-use of the solvent (THF) adds additional steps in the synthetic process with BMS.

Amine-boranes have also been made via transamination.[6] The equilibrium in this protocol depends on the nucleophilicity of the incoming amine and can be shifted towards a particular amine-borane by distillation of the volatile amine. One of the problems with this protocol is that the lower boiling amine is only partly removed, thus preventing the completion of the reaction. In certain cases, attempted distillation of the liquid residue has been reported to explode violently.[6] Synthesis of amine- and phosphine-boranes from metal hydrides[7] and borohydrides[8] has also been reported.

Exchange reaction of amine-boranes with phosphines is also known. Hawthorne and coworkers examined the kinetics of the displacement reaction of trialkylamine-boranes with phosphines and proposed an $S_N2$ mechanism at the tetrahedral boron center ($S_N2B$).[9] The $S_N2B$ reaction kinetics for the amine exchange of ammonia borane (AB, 1) with N,N,N-triethylamine ($Et_3N$) in a flame-sealed NMR tube at 35° C., without a preparative procedure, has been recently described.[10]

Depending on the strength of the complexes, a variety of applications have been found for amine-boranes.[1] They have been utilized for reduction of carbonyls,[11] reductive amination,[12] hydrogenation of olefins,[13] metal-free hydroboration of alkenes,[14] curing agents in epoxy resin preparation,[15] preparation of lithium aminoborohydrides,[16] or as pharmacologically active moieties,[17] etc. Most recently, amine-boranes have gained significance as hydrogen storage materials[18] and hypergolic propellants.[19]

We had recently reported a near quantitative and safe preparation of a series of aliphatic amine- and phosphine-boranes from AB in refluxing THF via the nucleophilic displacement of ammonia (Scheme 1).[20] The volatility of ammonia was exploited during the synthesis.

Scheme 1. Synthesis of amine-borane via trans-amination in refluxing THF.

Large-scale synthesis of ammonia borane became a necessity for the preparation of multi-gram quantities of amine-boranes. The required ammonia borane was prepared in large-scale from sodium borohydride (SBH) and powdered ammonium sulfate in reagent-grade THF containing 5% dissolved ammonia at ambient temperature and pressure (Scheme 2).[21]

Scheme 2. Synthesis of ammonia borane in ammoniated THF.

Other procedures to prepare ammonia borane involve the following:

The reaction of SBH and ammonium sulfate under ambient conditions in THF at low concentrations (0.165 M, Scheme 3).[22] The high dilution inhibited large-scale preparation. This problem was overcome with an improved synthesis using ammonium formate and SBH in 1 M dioxane (Scheme 4). However, (i) the carcinogenicity of dioxane, (ii) the tedious removal of solvent for recycling, and (iii) the cost of the anhydrous solvent again posed obstacles.

Scheme 3. Synthesis of ammonia borane in dilute THF.

Autrey and coworkers have reported the synthesis of AB from SBH and ammonium chloride in liquid ammonia at −78° C. via THF-mediated decomposition of the in situ generated ammonium borohydride.[23] The scale-up of this protocol requires the condensation of large quantities of ammonia. Their reported modification of the metathesis of $NaBH_4$ and $NH_4Cl$ in ammonia, followed by the addition of THF is carried out using a Hastelloy reactor. These procedures require anhydrous solvent, low temperature or a special apparatus, thus making the scale-up inconvenient.

Scheme 4. Ammonia borane synthesis in dioxane.

More recently, Shore and coworkers reported a large-scale synthesis of AB from either borane-methyl sulfide (BMS) or N,N-dimethylaniline-borane via the nucleophilic displacement of the base with gaseous ammonia in anhydrous THF or toluene.[24] The former borane complex (BMS) is expensive, pyrophoric, has an obnoxious odor and is synthesized from SBH using corrosive $BF_3$-etherate. The latter complex (N,N-dimethylaniline-borane) is prepared by passing gaseous diborane, generated in situ from SBH and $I_2$ in diglyme, through N,N-dimethylaniline in toluene (Scheme 5). All of the above mentioned processes are carried out in dry solvents, under an inert atmosphere adding to the cost of AB.

Scheme 5. Synthesis of ammonia borane via displacement reaction.

There is therefore an unmet need for novel methods for making ammonia borane and amine-boranes.

SUMMARY

In one aspect, a method for preparing ammonia borane is disclosed. The method includes the step of reacting a stoichiometric amount of sodium borohydride and twice the stoichiometric amount of ammonium salt in tetrahydrofuran (THF) at room temperature, the THF containing about 1% dissolved water. The reaction is conducted at room temperature.

In another aspect, a method for preparing amine-boranes is disclosed. The method includes the step of reacting a stoichiometric amount of sodium borohydride with a stoichiometric amount of ammonium salt in refluxing THF in the presence of at least one corresponding amine.

In yet another aspect, a method for preparing amine-boranes is disclosed. The method includes the step of adding a solution of THF containing about a slight excess than stoichiometric amount of water to a mixture. The mixture includes a slight excess than stoichiometric amount of sodium borohydride, a corresponding amine, and a slight excess than stoichiometric amount of sodium bicarbonate. The reaction is conducted at room temperature.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Disclosed herein are novel procedures to make ammonia borane and amine-boranes.

Past experience in preparing ammonia borane (AB) in ammoniated THF[21] indicated that the presence of $NH_3$ in the medium accelerates the rate of the reaction and prevents the formation diammoniate of diborane (DADB) byproduct. As disclosed herein, water can also be used for a similar reaction. Due to the stability of SBH and AB in water, as further disclosed herein, this has led to the simplest possible synthesis of ammonia borane from sodium borohydride.

Upon mixing SBH and the ammonium salt in THF at 0° C., very little or no reaction takes place. However, addition of 1% water initiates an exothermic reaction, which leads to the formation of ammonia borane. The solids are separated by filtration and washed with THF. Removal of THF form the filtrate provides moderate yields of AB. Analysis by $^{11}B$ NMR spectroscopy as well as hydrolysis revealed the product to be 99% pure.

In one embodiment, a novel procedure to prepare ammonia borane in large quantities has been developed, which involves an instantaneous reaction of sodium borohydride and ammonium sulfate in THF containing 1% dissolved water (Scheme 6).

Scheme 6. Facile synthesis of ammonia borane.

The synthesis of amine-boranes from AB prompted us to examine the possibility of generating AB in situ and its conversion to amine-boranes. Accordingly, we have developed a one-pot procedure for the preparation of amine-boranes from sodium borohydride.

The procedure involves the reaction of sodium borohydride and ammonium salts in refluxing THF in the presence of the corresponding amines (Scheme 7). This reaction likely involves an amine-salt exchange-metathesis cascade.

Scheme 7. Direct Synthesis of amine-boranes from sodium borohydride in refluxing THF.

In another embodiment, we envisaged the synthesis of amine-boranes from sodium borohydride and MHX (M=Na, K) salts in the presence of amines. Thus, another procedure for amine-borane synthesis involves the addition of THF containing 7.2% water to a mixture of sodium borohydride, the corresponding amine, and sodium bicarbonate (Scheme 8). This reaction is carried out at room temperature and is complete within 4-8 h. Other MHX salts, such as sodium bisulfate, sodium bisulfite, etc. can be used for this reaction.

Scheme 8. Preparation of amine-boranes at room temperature.

Example 1: Water Promoted Ammonia Borane Synthesis

Experimental:

The $^{11}$B NMR spectra were recorded using a Varian Inova-300 spectrometer (96 MHz) with a Nalorac quad probe and were referenced to $BF_3 \cdot OEt_2$ (0.0 ppm) as an external standard. Tetrahydrofuran (THF, ACS grade containing 0.004% water and 0.025% BHT) was purchased from Fisher-Scientific. Sodium borohydride (powder, purity >99% by hydride estimation) was purchased in bulk from Dow Chemical Co. (Rohm and Haas). Ammonium sulfate (ACS reagent, Mallinckrodt) was purchased from the respective commercial source and powdered prior to use.

In a typical reaction procedure, sodium borohydride (37.83 g, 1 mol) and powdered ammonium sulfate (132.14 g, 1 mol) were transferred to a 3 L three-neck round bottom flask fitted with an overhead stirrer. The flask was cooled in an ice-water bath and reaction contents carefully stirred. 1 L reagent-grade THF was then added to the flask followed by the dropwise addition of 10 mL water (1% v/v of THF). On completion of water addition, the reaction contents were warmed to room temperature and vigorously stirred. Upon completion of the reaction (4 h), as monitored by $^{11}$B NMR spectroscopy, the reaction contents were filtered through celite, and the residue washed with THF. The combined filtrate was concentrated under vacuum to obtain ammonia borane (20.99 g, 68%) at 99% chemical purity, as determined by both $^{11}$B NMR spectroscopy (δ -22.1 ppm (q)) and hydride analysis.

Example 2: Open-Flask Synthesis of Amine-Boranes Via Tandem Amine-Ammonium Salt Equilibration-Metathesis The past decade has seen amine-boranes receive considerable attention because of their potential as safe carriers of hydrogen for energy storage.[18] In addition to their traditional use as borane carriers for exchange reactions, applications as precursors to high-performance polymers via catalytic dehydrocoupling[25] and as reagents for novel organic transformations have made them even more relevant.[11-16] They have also gained significance as reagents of choice for the syntheses of metal nanoparticles[26] and nucleic acid analogues.[27] Recently, we reported on the prospect of amine-boranes as hypergolic bipropellants with consistently low ignition delays.[19] This finding led us to the decades-old quest to replace toxic hydrazine and its derivatives as hypergolic fuels for space and missile applications. To expand our study, the preparation of large quantities of a variety of amine-boranes became a necessity.

The repeated large-scale preparation of ammonia borane (AB) to obtain multi-gram quantities of the corresponding amine-boranes via transamination[20] (Scheme 9) hampered progress. This prompted us to adopt or develop a direct synthesis of amine-boranes. However, the reported metathesis of ammonium salts with sodium borohydride (SBH)[28] lacks generality because of the poor solubility of SBH and alkylammonium salts in common ether solvents, such as diethyl ether ($Et_2O$) and tetrahydrofuran (THF).[29] This is circumvented by using either more reactive, but flammable lithium borohydride[30] or SBH in dimethoxyethane,[31] adding to the cost of the product. Also, the lack of commercial availability of the necessary amine salts restricts its wide applicability.

Scheme 9. Transamination of AB

Additives such as 18-crown-6 have been used to catalyze the reaction in $Et_2O$.[32] Another reported modification involves addition of organic acids to prepare specific amine-boranes.[33]

With in situ AB synthesis, followed by transamination (Scheme 10), being envisioned, 1 equiv. each of SBH, ammonium sulfate, and N,N,N-triethylamine (TEA, 1a) were refluxed in 1M THF. All of SBH was consumed within 1 h, and we were delighted to observe, by $^{11}$B NMR spectroscopy, the formation of 99% TEA-borane (TEAB, 2a) and 1% AB (Table 1, entry 1).

Scheme 10. Proposed in situ AB synthesis-transamination sequence

TABLE 1

Effect of the Temperature on the TEAB Synthesis$^a$

| Entry | time (h) | temperature (° C.) | TEAB:AB$^b$ |
|---|---|---|---|
| 1 | 1 | Reflux | 99:1 |
| 2 | 4 | Reflux | 100:0 |
| 3 | 1 | rt | 85:15 |
| 4 | 4 | rt | 85:15 |
| 5 | 24 | rt | 86:14 |
| 6 | 1 | 40 | 88:12 |

TABLE 1-continued

Effect of the Temperature on the TEAB Synthesis[a]

| Entry | time (h) | temperature (° C.) | TEAB:AB[b] |
|---|---|---|---|
| 7 | 4 | 40 | 88:12 |
| 8 | 24 | 40 | 91:9 |

[a]Reactions were performed using 5 mmol each of SBH, $(NH_4)_2SO_4$ and $Et_3N$ in 5 mL THF, open to air.
[b]Based on the $^{11}B$ NMR spectra of reaction aliquots.

Continued refluxing for an additional 3 h converted the traces of AB to TEAB (Table 1, entry 2). Filtering off the solids and removing the solvent provided 90% yield of pure 2a ($^{11}B$, $^{1}H$, and $^{13}C$ NMR and hydride analysis). Notably, no dehydrogenation byproducts were observed even in the presence of mildly acidic $(NH_4)_2SO_4$.

Unexpectedly, when the reaction was carried out in THF at room temperature (rt; Scheme 11), all of SBH was consumed within 1 h, with the concurrent evolution of 1 equiv of $H_2$. Spectroscopic analysis revealed the formation of a mixture of TEAB and AB in a 17:3 ratio, which remained essentially unchanged over the next 3 h (Table 1, entries 3 and 4), suggesting that the reaction could not have proceeded via the formation of AB as envisioned in Scheme 10. The extremely slow transamination of AB with TEA even after 24 h at rt (Table 1, entry 5) formed the basis for this assumption. Monitoring the reaction temperature inside the flask revealed negligible change, thus negating its role in the reaction progress. The formation of TEAB at rt (Scheme 11) can only be rationalized by invoking an amine-ammonium salt equilibrium,[34] followed by salt metathesis of triethylammonium sulfate with SBH (Scheme 12). Under reflux conditions, either the amine-salt exchange is facilitated or any AB formed undergoes facile transamination with the remaining TEA. Refluxing is essential because maintaining the temperature at 40° C.[35] resulted only in a 91:9 mixture of TEAB and AB in 24 h (Table 1, entry 8) (note: the reaction was attempted at 40° C. with prior knowledge of AB synthesis at this temperature[21]). Extended refluxing does not deteriorate TEAB ($^{11}B$ NMR spectroscopy). The stability of TEAB may allow for its potential use in on-demand AB production.

Scheme 11. Room Temperature Formation of a TEAB-AB Mixture

Scheme 12. Tandem amine-ammonium salt equilibration metathesis

Several ammonium salts, such as ammonium chloride, fluoride, formate, and carbonate, were then scanned for the salt-exchange reaction under varying conditions. The results, summarized in Table 2, show that ammonium chloride and sulfate provide the best outcomes (entries 1 and 9), with the reaction with the latter being faster. Significantly, the reaction stoichiometry revealed that, unlike for the AB synthesis where 2 equiv. of ammonium ion were necessary, herein 1 equiv. is sufficient to achieve optimal yields, thus decreasing the overall cost of the process. The reaction is extremely slow in refluxing $Et_2O$, requiring 4 days for completion (Table 2, entry 13). The optimal concentration for best yields and fast reaction (Table 2, entry 10, highlighted in boldface) is 1 M THF.

TABLE 2

Optimization of Conditions for the Preparation of TEAB from SBH[a]

| entry | $NH_4X$ | $SBH:NH_4X$ | time (h) | yield[b] (%) |
|---|---|---|---|---|
| 1 | $NH_4Cl$ | 1:2 | 8 | 87 |
| 2 | $NH_4Cl$ | 1:1 | 20[c] | 67 |
| 3 | $NH_4F$ | 1:2 | 4 | 97[d] |
| 4 | $NH_4F$ | 1:1 | 2 | 74[d] |
| 5 | $NH_4OCOH$ | 1:2 | 4 | 110[e] |
| 6 | $NH_4OCOH$ | 1:1 | 3 | 71[e] |
| 7 | $(NH_4)_2CO_3$ | 1:1 | 6 | 78 |
| 8 | $(NH_4)_2CO_3$ | 2:1 | 20[c] | 53 |
| 9 | $(NH_4)_2SO_4$ | 1:1 | 4 | 90 |
| 10 | $(NH_4)_2SO_4$ | 2:1 | 6 | 90 |
| 11 | $(NH_4)_2SO_4$ | 2:1 | 4[f] | 85 |
| 12 | $(NH_4)_2SO_4$ | 2:1 | 16[g] | 92 |
| 13 | $(NH_4)_2SO_4$ | 2:1 | 96[h] | 88 |

[a]Reactions were performed using 5 mmol each of SBH and $Et_3N$ in 5 mL of solvent under reflux, open to air.
[b]Isolated yield.
[c]Peaks corresponding to trace quantities of SBH were present in the $^{11}B$ NMR spectrum.
[d]96% purity ($^{11}B$ NMR).
[e]Product contains triethylammonium formate impurity.
[f]2M reaction.
[g]4M reaction.
[h]Reaction in $Et_2O$.

Having standardized the conditions for TEAB synthesis, the protocol was applied to a variety of 1°, 2°, and 3° alkylamines to demonstrate its generality as well as to prepare all of the amine-boranes necessary for our project. As can be seen from Table 3, most alkylamines gave excellent yields of the corresponding amine-boranes (2a-2f, entries 1-6). Because of the distinct advantages of diamine-bisboranes as potential hybrid rocket fuels,[36] 1°, 2°, and 3° diamines were included in our study and the corresponding bisboranes were isolated in high yields (2g-2i, entries 7-9). Heteroarylamines, such as pyridine (1j) and 2-picoline (1k), yielded the corresponding borane adducts (2j and 2k, respectively, entries 10 and 11) in near quantitative yields.

TABLE 3

Synthesis of Amine-Boranes from SBH[a]

$$2NaBH_4 + (NH_4)_2SO_4 \xrightarrow[\text{reflux}]{\underset{\text{THF, 1M}}{2(H_{3-n})R_n\ddot{N}}} 2(H_{3-n})R_nN-BH_3 + 2\ddot{N}H_3 + Na_2SO_4 + H_2\uparrow$$

n = 1,2,3

| Entry | Amine no | Amine | time (h) | amine-borane no | yield[b] (%) |
|---|---|---|---|---|---|
| 1 | 1a | Et₂NEt (triethylamine) | 6 | 2a | 90 |
| 2 | 1b | tert-butylamine | 6 | 2b | 93 |
| 3 | 1c | cyclohexylamine | 6 | 2c | 98 |
| 4 | 1d | diisopropylamine | 6 | 2d | 80 |
| 5 | 1e | morpholine | 6 | 2e | 98 |
| 6 | 1f | N-ethylpiperidine | 6 | 2f | 87 |
| 7 | 1g | H₂N–CH₂CH₂–NH₂ | 8 | 2g | 83[c] |
| 8 | 1h | piperazine | 8 | 2h | 82 |
| 9 | 1i | N,N'-dimethylpiperazine | 8 | 2i | 97[d] |
| 10 | 1j | pyridine | 8 | 2j | 99 |
| 11 | 1k | 2-methylpyridine | 8 | 2k | 93 |

[a]Reactions were performed using 5 mmol of SBH, 2.5 mmol of (NH₄)₂SO₄, and 5 mmol of amine/2.5 mmol of diamine in 5 mL THF under reflux, open to air.
[b]Isolated yield.
[c]See SI.
[d]A mixture of diastereomers.

This example serves to demonstrate an economical protocol to prepare a variety of aliphatic and heteroarylamine-boranes in excellent yields directly from SBH and the corresponding amines. In addition to the wide substrate scope, the described amine-ammonium salt equilibrium-metathesis protocol has several significant benefits: (i) open-flask conditions; (ii) atom economical use of stoichiometric ammonium sulfate; (iii) use of reagent-grade THF; (iv) no tedious purification required beyond filtration; (v) recovery and recycling of the solvent over multiple runs. The viability of this convenient preparation of amine-boranes, demonstrated with a mole-scale synthesis of TEAB (2a), should make them readily available and aid the advancement of hydrogen energy and propellant research. In addition, this can also find applications in the synthesis of 1° aminoborane-derived borazines.[37] Supporting information is herein incorporated by reference (entry 38 below).

Experimental:

$^{11}$B, $^{1}$H, and $^{13}$C NMR spectra were recorded at room temperature, on a Varian INOVA 300 MHz NMR spectrophotometer. Chemical shifts (δ values) are reported in parts per million relative to $BF_3.Et_2O$ for $^{11}$B NMR respectively. Data are reported as: δ value, multiplicity (s=singlet, d=doublet, t=triplet, q=quartet, p=pentet, h=hextet, m=multiplet, br=broad) and integration. Tetrahydrofuran (THF, ACS grade containing 0.004% water and 0.025% BHT) was purchased from Fisher-Scientific. Sodium borohydride (SBH, powder, purity >99% by hydride estimation) was purchased in bulk from Dow Chemical Co. (Rohm and Haas). Ammonium fluoride (98%, Sigma-Aldrich), ammonium chloride (ACS reagent, Mallinckrodt), ammonium formate (97%, Sigma-Aldrich), ammonium sulfate (ACS reagent, Mallinckrodt), and ammonium carbonate (ACS reagent, Sigma-Aldrich) were purchased from the respective commercial sources and powdered prior to use. All of the amines used were purchased from commercial sources. Liquid amines were distilled while solid amines were used without any purification. All of the amine-boranes (2a-2k) synthesized have been reported in prior literature.

General Procedure for the Preparation of Amine-Boranes (2a-2k):

SBH (0.19 g, 5 mmol) and powdered ammonium sulfate (0.33 g, 2.5 mmol) were transferred to a 25 mL dry round bottom flask, fitted with a water-cooled reflux condenser. The corresponding amine (1a-1f, 1j-1k, 5 mmol) or diamine (1g-1i, 2.5 mmol) was charged into the reaction flask followed by addition of THF (5 mL) at rt. The heterogeneous reaction mixture was brought to reflux, under vigorous stirring. Reaction progress was monitored by $^{11}$B NMR spectroscopy (Note: A drop of anhydrous DMSO is added to the reaction aliquot before running the NMR experiment). Upon completion of the reaction (6-8 h), the reaction contents were cooled to rt, filtered through celite, and washed with THF. Removal of solvent from the filtrate in vacuo yielded the corresponding amine-borane.

Procedure for the Large-Scale Preparation of N,N,N-Triethylamine-Borane (2a):

The reaction was carried out in a well-ventilated hood with the reaction vessel outlet directly leading into the hood exhaust due to the hazards associated with escaping ammonia and the liberation of large quantities of hydrogen.

Sodium borohydride (37.9 g, 1 mol) and powdered ammonium sulfate (66.1 g, 0.5 mol) were transferred to a 3-necked 3 L dry round bottom flask, fitted with water-cooled reflux condensers. N,N,N-Triethylamine (1a, 139.4 mL, 1 mol) was charged into the flask, followed by THF (1 L) at rt. The heterogeneous reaction mixture was brought to reflux, under vigorous stirring. Upon completion of the reaction (6 h), as monitored by $^{11}$B NMR spectroscopy, the reaction contents were cooled to rt, filtered through celite, and washed with THF. Removal of solvent from the filtrate in vacuo yielded 2a as a colorless liquid (103.5 g, 90%). Hydride analysis revealed 2a to be 97% pure.

$^{1}$H NMR (300 MHz, CDCl$_3$) δ (ppm): 2.79 (qd, J=7.4, 1.7 Hz, 6H), 1.19 (td, J=7.3, 1.7 Hz, 9H), 2.10-0.9 (br q, BH$_3$); $^{13}$C NMR (75 MHz, CDCl$_3$) δ (ppm): 52.2, 8.6. $^{11}$B NMR (96 MHz, CDCl$_3$) δ (ppm): −13.95 (q, J=96.0 Hz).

General Procedure for Hydride Analysis of Amine-Boranes (Hydrolysis Reaction):

An aqueous solution of amine-borane (2 mmol in 1 mL H$_2$O) was transferred to a round bottom flask with a septum inlet fitted with a connecting tube. The connecting tube was attached to an analytical gas burette filled with CuSO$_4$ solution. A solution of RuCl$_3$ (4.2 mg, 1 mol % in 2 mL H$_2$O) was syringed into the vial, all at once. The hydrogen generated was measured using the analytical gas burette. The temperature of the reaction was maintained at 25° C.

Experimental Procedures and Characterization of Amine-Boranes:

N,N,N-Triethylamine-Borane (2a):

SBH (0.19 g, 5 mmol) and powdered ammonium sulfate (0.33 g, 2.5 mmol) were transferred to a 25 mL dry round bottom flask charged with a magnetic stir-bar and fitted with a water-cooled reflux condenser. N,N,N-Triethylamine (1a, 0.7 mL, 5 mmol) was charged into the reaction flask followed by addition of THF (5 mL) at rt. The heterogeneous reaction mixture was brought to reflux, under vigorous stirring. Reaction progress was monitored by $^{11}$B NMR spectroscopy (Note: A drop of anhydrous DMSO is added to the reaction aliquot before running the NMR experiment). Upon completion of the reaction (6 h), the reaction contents were cooled to rt, filtered through celite, and the residue was washed with THF. Removal of solvent from the filtrate in vacuo yielded N,N,N-triethylamine-borane (2a) as a colorless liquid (0.52 g, 90%).

$^{1}$H NMR (300 MHz, CDCl$_3$) δ (ppm): 2.79 (qd, J=7.4, 1.7 Hz, 6H), 1.19 (td, J=7.3, 1.7 Hz, 9H), 2.10-0.9 (br q, BH$_3$); $^{13}$C NMR (75 MHz, CDCl$_3$) δ (ppm): 52.2, 8.6. $^{11}$B NMR (96 MHz, CDCl$_3$) δ (ppm): −13.95 (q, J=96.0 Hz).

tert-Butylamine-borane (2b):

SBH (0.19 g, 5 mmol) and powdered ammonium sulfate (0.33 g, 2.5 mmol) were transferred to a 25 mL dry round bottom flask charged with a magnetic stir-bar and fitted with a water-cooled reflux condenser. tert-Butylamine (1b, 0.53 mL, 5 mmol) was charged into the reaction flask followed by addition of THF (5 mL) at rt. The heterogeneous reaction mixture was brought to reflux, under vigorous stirring. Reaction progress was monitored by $^{11}$B NMR spectroscopy (Note: A drop of anhydrous DMSO is added to the reaction aliquot before running the NMR experiment). Upon completion of the reaction (6 h), the reaction contents were cooled to rt, filtered through celite, and the residue was washed with THF. Removal of solvent from the filtrate in vacuo yielded tert-butylamine-borane (2b) as a white solid (0.40 g, 93%).

$^{1}$H NMR (300 MHz, CDCl$_3$) δ (ppm): 3.81 (s, 2H), 1.22 (s, 9H), 2.0-0.7 (br q, BH$_3$); $^{13}$C NMR (75 MHz, CDCl$_3$) δ (ppm): 51.9, 26.8; $^{11}$B NMR (96 MHz, CDCl$_3$) δ (ppm): −23.35 (q, J=93.9 Hz).

Cyclohexylamine-Borane (2c):

SBH (0.19 g, 5 mmol) and powdered ammonium sulfate (0.33 g, 2.5 mmol) were transferred to a 25 mL dry round bottom flask charged with a magnetic stir-bar and fitted with a water-cooled reflux condenser. Cyclohexylamine (1c, 0.57 mL, 5 mmol) was charged into the reaction flask followed by addition of THF (5 mL) at rt. The heterogeneous reaction mixture was brought to reflux, under vigorous stirring. Reaction progress was monitored by $^{11}$B NMR spectroscopy (Note: A drop of anhydrous DMSO is added to the reaction aliquot before running the NMR experiment). Upon completion of the reaction (6 h), the reaction contents were cooled to rt, filtered through celite, and the residue was washed with THF. Removal of solvent from the filtrate in vacuo yielded cyclohexylamine-borane (2c) as a white solid (0.55 g, 98%).

$^1$H NMR (300 MHz, CDCl$_3$) δ (ppm): 3.59 (s, 2H), 2.72 (tdt, J=10.4, 7.7, 3.0 Hz, 1H), 2.22-2.09 (m, 2H), 1.86-1.57 (m, 3H), 1.42-1.06 (m, 5H)), 0.90-2.05 (br q, BH$_3$); $^{13}$C NMR (75 MHz, CDCl$_3$) δ (ppm): 56.8, 32.2, 25.2, 24.4; $^{11}$B NMR (96 MHz, CDCl$_3$) δ (ppm): −20.88 (q, J=95.0 Hz).

N,N-Diisopropylamine-Borane (2d):

SBH (0.19 g, 5 mmol) and powdered ammonium sulfate (0.33 g, 2.5 mmol) were transferred to a 25 mL dry round bottom flask charged with a magnetic stir-bar and fitted with a water-cooled reflux condenser. N,N-Diisopropylamine (1d, 0.7 mL, 5 mmol) was charged into the reaction flask followed by addition of THF (5 mL) at rt. The heterogeneous reaction mixture was brought to reflux, under vigorous stirring. Reaction progress was monitored by $^{11}$B NMR spectroscopy (Note: A drop of anhydrous DMSO is added to the reaction aliquot before running the NMR experiment). Upon completion of the reaction (6 h), the reaction contents were cooled to rt, filtered through celite, and the residue was washed with THF. Removal of solvent from the filtrate in vacuo yielded N,N-diisopropylamine-borane (2d) as a colorless liquid (0.46 g, 80%).

$^1$H NMR (300 MHz, CDCl$_3$) δ (ppm): 3.39-3.11 (m, 3H), 1.28 (ddd, J=6.7, 5.1, 1.8 Hz, 12H), 0.70-2.00 (br q, BH$_3$); $^{13}$C NMR (75 MHz, CDCl$_3$) δ (ppm): 51.9, 18.9, 20.9; $^{11}$B NMR (96 MHz, CDCl$_3$) δ (ppm): −21.76 (q, J=96.0 Hz).

Morpholine-Borane (2e):

SBH (0.19 g, 5 mmol) and powdered ammonium sulfate (0.33 g, 2.5 mmol) were transferred to a 25 mL dry round bottom flask charged with a magnetic stir-bar and fitted with a water-cooled reflux condenser. Morpholine (1e, 0.44 mL, 5 mmol) was charged into the reaction flask followed by addition of THF (5 mL) at rt. The heterogeneous reaction mixture was brought to reflux, under vigorous stirring. Reaction progress was monitored by $^{11}$B NMR spectroscopy (Note: A drop of anhydrous DMSO is added to the reaction aliquot before running the NMR experiment). Upon completion of the reaction (6 h), the reaction contents were cooled to rt, filtered through celite, and the residue was washed with THF. Removal of solvent from the filtrate in vacuo yielded morpholine-borane (2e) as a white solid (0.49 g, 98%).

$^1$H NMR (300 MHz, CDCl$_3$) δ (ppm): 4.38 (s, 1H), 3.95-3.75 (m, 2H), 3.53 (t, J=12.3 Hz, 2H), 3.03 (d, J=13.5 Hz, 2H), 2.83-2.63 (m, 2H), 1.5 (br q, 3H, BH$_3$); $^{13}$C NMR (75 MHz, CDCl$_3$) δ (ppm): 64.5, 50.8; $^{11}$B NMR (96 MHz, CDCl$_3$) δ −15.47 (q, J=97.2 Hz).

N-Ethylpiperidine-Borane (2f):

SBH (0.19 g, 5 mmol) and powdered ammonium sulfate (0.33 g, 2.5 mmol) were transferred to a 25 mL dry round bottom flask charged with a magnetic stir-bar and fitted with a water-cooled reflux condenser. N-Ethylpiperidine (1f, 0.69 mL, 5 mmol) was charged into the reaction flask followed by addition of THF (5 mL) at rt. The heterogeneous reaction mixture was brought to reflux, under vigorous stirring. Reaction progress was monitored by $^{11}$B NMR spectroscopy (Note: A drop of anhydrous DMSO is added to the reaction aliquot before running the NMR experiment). Upon completion of the reaction (6 h), the reaction contents were cooled to rt, filtered through celite, and the residue was washed with THF. Removal of solvent from the filtrate in vacuo yielded N-ethylpiperidine-borane (2f) as a colorless liquid (0.55 g, 87%).

$^1$H NMR (300 MHz, CDCl$_3$) δ (ppm): 3.03-2.80 (m, 4H), 2.80-2.67 (m, 2H), 1.94-1.78 (m, 2H), 1.70-1.49 (m, 4H), 1.27 (t, J=7.2 Hz, 3H), 2.10-0.95 (br q, BH$_3$); $^{13}$C NMR (75 MHz, CDCl$_3$) δ (ppm): 57.4, 54.6, 22.7, 20.3, 8.8; $^{11}$B NMR (96 MHz, CDCl$_3$) δ (ppm): −13.01 (q, J=97.0 Hz).

1,2-Diaminoethane-Bisborane (2g):

SBH (0.19 g, 5 mmol) and powdered ammonium sulfate (0.33 g, 2.5 mmol) were transferred to a 25 mL dry round bottom flask charged with a magnetic stir-bar and fitted with a water-cooled reflux condenser. 1,2-Diaminoethane (1g, 0.17 mL, 2.5 mmol) was charged into the reaction flask followed by addition of THF (5 mL) at rt. The heterogeneous reaction mixture was brought to reflux, under vigorous stirring. Reaction progress was monitored by $^{11}$B NMR spectroscopy (Note: A drop of anhydrous DMSO is added to the reaction aliquot before running the NMR experiment). Upon completion of the reaction (8 h), the reaction contents were cooled to rt, filtered through celite, and the residue was washed with THF. Removal of solvent from the filtrate in vacuo yielded a crude solid which was further purified by washing with isopropanol and water to yield 1,2-diaminoethane-bisborane (2g) as a white solid (0.18 g, 83%).

$^1$H NMR (300 MHz, DMSO-d$_6$) δ (ppm): 5.25 (s, 4H), 2.61 (s, 4H), 2.11-0.23 (br s, 6H, BH$_3$); $^{13}$C NMR (75 MHz, DMSO-d$_6$) δ (ppm): 45.8; $^{11}$B NMR (96 MHz, THF) δ (ppm): −19.29 (q, J=95.0 Hz).

Piperazine-Bisborane (2h):

SBH (0.19 g, 5 mmol) and powdered ammonium sulfate (0.33 g, 2.5 mmol) were transferred to a 25 mL dry round bottom flask charged with a magnetic stir-bar and fitted with a water-cooled reflux condenser. Piperazine (1h, 0.22 g, 2.5 mmol) was charged into the reaction flask followed by addition of THF (5 mL) at rt. The heterogeneous reaction mixture was brought to reflux, under vigorous stirring. Reaction progress was monitored by $^{11}$B NMR spectroscopy (Note: A drop of anhydrous DMSO is added to the reaction aliquot before running the NMR experiment). Upon completion of the reaction (8 h), the reaction contents were cooled to rt, filtered through celite, and the residue was washed with THF. Removal of solvent from the filtrate in vacuo yielded piperazine-bisborane (2h) as a white solid (0.23 g, 82%).

$^1$H NMR (300 MHz, DMSO-d$_6$) δ (ppm): 6.19 (s, 2H), 3.20-2.77 (m, 4H), 2.75-2.42 (m, 4H), 2.15-0.62 (br q, 6H); $^{13}$C NMR (75 MHz, DMSO-d$_6$) δ (ppm): 49.9; $^{11}$B NMR (96 MHz, DMSO-d$_6$) δ (ppm): −10.30 (q, J=95.0 Hz).

N,N-Dimethylpiperazine-Bisborane (2i):

SBH (0.19 g, 5 mmol) and powdered ammonium sulfate (0.33 g, 2.5 mmol) were transferred to a 25 mL dry round bottom flask charged with a magnetic stir-bar and fitted with a water-cooled reflux condenser. N,N-Dimethylpiperazine (1i, 0.34 mL, 2.5 mmol) was charged into the reaction flask followed by addition of THF (5 mL) at rt. The heterogeneous reaction mixture was brought to reflux, under vigorous stirring. Reaction progress was monitored by $^{11}$B NMR spectroscopy (Note: A drop of anhydrous DMSO is added to the reaction aliquot before running the NMR experiment). Upon completion of the reaction (8 h), the reaction contents were cooled to rt, filtered through celite, and the residue was washed with THF. Removal of solvent from the filtrate in vacuo yielded N,N-dimethylpiperazine-bisborane (2i) as a white solid (0.34 g, 97%) as a mixture of diastereomers (from $^{11}$B NMR analysis).

$^1$H NMR (300 MHz, DMSO-d$_6$) δ (ppm): 3.22-2.68 (m), 2.69-2.45 (m), 2.46-2.30 (m), 2.22 (d, J=1.7 Hz), 2.15-0.79 (br, BH$_3$); $^{13}$C NMR (75 MHz, DMSO-d$_6$) δ (ppm): 54.0, 53.7; $^{11}$B NMR (96 MHz, THF) δ (ppm): −9.97 (q), −11.89 (q). The two quartets are merged, which are separated into two singlets upon $^1$H-$^{11}$B decoupling.

Pyridine-Borane (2j):

SBH (0.19 g, 5 mmol) and powdered ammonium sulfate (0.33 g, 2.5 mmol) were transferred to a 25 mL dry round bottom flask charged with a magnetic stir-bar and fitted with a water-cooled reflux condenser. Pyridine (1j, 0.40 mL, 5 mmol) was charged into the reaction flask followed by addition of THF (5 mL) at rt. The heterogeneous reaction mixture was brought to reflux, under vigorous stirring. Reaction progress was monitored by $^{11}$B NMR spectroscopy (Note: A drop of anhydrous DMSO is added to the reaction aliquot before running the NMR experiment). Upon completion of the reaction (8 h), the reaction contents were cooled to rt, filtered through celite, and the residue was washed with THF. Removal of solvent from the filtrate in vacuo yielded pyridine-borane (2j) as a colorless liquid (0.46 g, 99%).

$^1$H NMR (300 MHz, CDCl$_3$) δ (ppm): 8.57 (d, J=5.5 Hz, 2H), 7.95 (td, J=7.7, 1.6 Hz, 1H), 7.59-7.48 (m, 2H), 2.62 (q, J=96 Hz, 3H, BH$_3$); $^{13}$C NMR (75 MHz, CDCl$_3$) δ (ppm): 146.8, 138.8, 125.0; $^{11}$B NMR (96 MHz, CDCl$_3$) δ (ppm): −12.57 (q, J=97.7 Hz).

2-Picoline-Borane (2k):

SBH (0.19 g, 5 mmol) and powdered ammonium sulfate (0.33 g, 2.5 mmol) were transferred to a 25 mL dry round bottom flask charged with a magnetic stir-bar and fitted with a water-cooled reflux condenser. 2-Picoline (1k, 0.49 mL, 5 mmol) was charged into the reaction flask followed by addition of THF (5 mL) at rt. The heterogeneous reaction mixture was brought to reflux, under vigorous stirring. Reaction progress was monitored by $^{11}$B NMR spectroscopy (Note: A drop of anhydrous DMSO is added to the reaction aliquot before running the NMR experiment). Upon completion of the reaction (8 h), the reaction contents were cooled to rt, filtered through celite, and the residue was washed with THF. Removal of solvent from the filtrate in vacuo yielded 2-picoline-borane (2k) as a white solid (0.50 g, 93%).

$^1$H NMR (300 MHz, CDCl$_3$) δ (ppm): 8.72 (d, J=6 Hz, 1H), 7.89-7.72 (m, 1H), 7.36 (dd, J=7.7, 1.4 Hz, 1H), 7.28 (ddd, J=7.7, 6.1, 1.7 Hz, 1H), 3.10-1.80 (br q, BH$_3$), 2.75 (s, 3H); $^{13}$C NMR (75 MHz, CDCl$_3$) δ 157.2, 148.2, 139.0, 126.3, 122.0, 22.5; $^{11}$B NMR (96 MHz, CDCl$_3$) δ (ppm): −14.22 (q, J=97.9 Hz).

Example 3: Water Promoted Amine-Borane Synthesis

If mild acids such as carbonic acid can be generated in situ in the presence of the amine and sodium borohydride (SBH), the alkylammonium salt formed can undergo metathesis with SBH at rt. The environmentally benign, non-toxic, and inexpensive sodium bicarbonate (SBC)/water system can be ideal for the transformation. Water could play the dual role of generating carbonic acid and solubilizing SBH, ensuring *facile* metathesis with the alkylammonium bicarbonate salt. Key to the success of the reaction would be (i) capture of carbonic acid by amine prior to its ready decomposition to carbon dioxide and water and (ii) stability of SBH and amine-boranes to reaction conditions.[39] Details of such a water mediated protocol utilizing sodium bicarbonate are described herein (Scheme 13).

Scheme 13. Water promoted amine-borane synthesis

An equiv. each of SBH and N,N,N-triethylamine (TEA, Et$_3$N, 1a) and two equiv. of SBC were treated with 1:1 THF-water solution ensuring 1 M concentration. Gratifyingly, analysis of the reaction aliquot taken after an hour by $^{11}$B NMR spectroscopy revealed complete consumption of SBH and the presence of 77% TEAB and 23% of hydrolyzed borate salts. To avoid the hydrolyzed byproduct, stoichiometric quantity of water was added to a mixture of SBC, SBH, and TEA in 1 M THF (Table 4, entry 1). Within 4 h, TEAB was the lone product observed by $^{11}$B NMR spectroscopy. Filtration followed by removal of solvent in vacuo yielded 77% of pure TEAB ($^{11}$B, $^1$H, and $^{13}$C NMR and hydride analysis). Lowering the equivalents of SBC (Table 4, entry 2) led to higher reaction times and lower yields of 2a. Employing a saturated solution of SBC in water yielded only the hydrolysed by-product. Also, the order of addition was found to be critical as adding amine to a THF mixture of SBH and SBC containing water yielded none of the desired product.

TABLE 4

Optimization of reaction conditions for the preparation of TEAB from SBH and TEA[a]

| Entry | Salt | NaBH$_4$:Salt (equiv.) | Time (h) | Yield[b] (%) |
|---|---|---|---|---|
| 1 | NaHCO$_3$ | 1:2 | 4 | 77 |
| 2 | NaHCO$_3$ | 1:1 | 24[c] | 65 |
| 3 | Na$_2$CO$_3$ | 1:2 | 48[c] | 20 |
| 4 | NaHSO$_3$ | 1:2 | 24[c] | 70 |
| 5 | NaHSO$_4$ | 1:2 | 24 | Trace |
| 6 | KHCO$_3$ | 1:2 | 24 | 49 |
| 7 | K$_2$HPO$_4$ | 1:2 | 24[c] | 14 |
| 8 | KH$_2$PO$_4$ | 1:1 | 24[c] | 47 |
| 9 | KH$_2$PO$_4$ | 1:2 | 24[c] | 30 |
| 10 | NaHCO$_3$ | 1:2 | 4[d] | 79 |
| 11 | NaHCO$_3$ | 1:2 | 4[e] | 78 |
| 12 | NaHCO$_3$ | 1:2 | 6[f] | 74 |

[a]Reactions were performed using 5 mmol each of SBH and TEA and the corresponding equivalents of salt in 2.5 mL of THF at rt open to air. Water was added as a 3.6% solution in THF (2.5 mL).
[b]Yields of isolated product.
[c]SBH was present when reaction contents filtered (by 11B NMR spectroscopy).
[d]2M THF.
[e]4M THF.
[f]4M Diethyl ether.

Several readily available sodium and potassium salts which could provide mineral acids in situ were screened in an effort to improve the yield of 2a (Table 4). Sodium carbonate was used to gauge the necessity of a bicarbonate salt and it was found to be detrimental to both the yield and reaction time (entry 3). Other sodium salts screened in the study (entries 4-5) did not improve reaction yields. Switching to potassium salts (entries 6-9) likewise failed to provide promising results. The role of concentration and solvent was then examined (with 2 equiv. SBC). Increasing the reaction concentration to 2 M or 4 M marginally improved the yield to 79% and 78% respectively (entries 10-11). Switching solvents to diethyl ether did not afford any appreciable alteration (entry 12). 2 equivalents of SBC in 2 M THF were chosen to be the optimal conditions for further study (entry 10, highlighted in bold face).

The role of water is critical in promoting the reaction. A reaction without water, even after two days, yielded only traces of TEAB (Table 5, entry 1). Its added equivalents should, thus, have a significant effect on the reaction outcome. Adding 0.5 equiv. considerably slowed the reaction taking 24 h for completion while providing 2a in 82% yield (Table 5, entry 2). Increasing the equivalents to 2 dramatically reduced the reaction time to 1 h while yielding 82% TEAB (entry 4). Further increase only had detrimental effects on the reaction yield (entries 5-6).

TABLE 5

Effect of equivalents of water on the preparation of TEAB from SBH and SBC[a]

| Entry | Salt | Water (equiv.) | Time (h) | Yield[b] (%) |
|---|---|---|---|---|
| 1 | NaHCO$_3$ | None | 48 | Trace |
| 2 | NaHCO$_3$ | 0.5 | 24 | 81 |
| 3 | NaHCO$_3$ | 1 | 4 | 79 |
| 4 | NaHCO$_3$ | 2 | 1 | 82 |
| 5 | NaHCO$_3$ | 4 | 0.5 | 66 |
| 6 | NaHCO$_3$ | 1:1 (THF:H$_2$O) | 1 | NP[c] |

[a]Reactions were performed using 5 mmol each of SBH and TEA and 10 mmol of SBC in 2M THF at rt open to air. Water was added dropwise as a 14.4% solution in THF.
[b]Yields of isolated product.
[c]NP = No Product.

To comprehend the less than quantitative yields obtained during the process, the solid residue obtained after filtration of reaction contents was analysed by $^{11}$B NMR spectroscopy. Analysis in water showed the presence of borate salt (δ 8 ppm) which may have been formed by the hydrolysis of SBH under the reaction conditions.[39] To ensure complete conversion of amine to amine-borane and compensate for the loss of SBH, the effect of excess SBH was studied. Also, a high-boiling amine, 4-(dimethylamino)pyridine (DMAP, 1r), was chosen for the study to prevent losing any residual amine. As can be seen from the table (Table 6), the use of at least 1.5 equivalents of SBH (entry 3) led to complete conversion of DMAP-BH$_3$ in quantitative yields.

TABLE 6

Effect of SBH stoichiometry on reaction conversion[a]

| Entry | SBH:DMAP (equiv.) | Time (h) | Yield[b] (%) | 1x:2x[c] |
|---|---|---|---|---|
| 1 | 1:1 | 8 | 99 | 20:80 |
| 2 | 1.25:1 | 4 | 99 | 7:93 |
| 3 | 1.5:1 | 4 | 99 | 0:100 |
| 4 | 2:1 | 4 | 99 | 0:100 |

[a]Reactions were performed using 5 mmol of SBH and 10 mmol of SBC in 2M THF at rt open to air while varying the DMAP equivalents as necessary. Water was added dropwise as a 14.4% solution in THF.
[b]Yields of isolated product.
[c]By $^1$H NMR spectroscopy.

The standardized protocol (1.5 equiv. SBH, 3 equiv. SBC, 1 equiv. amine and 3 equiv. water in 2 M THF at rt), was applied to a variety of amines (Table 7). Primary amines propanamine (11), cyclohexylamine (1c), and tert-butylamine (1b) with varying substitution at the carbon center provided the corresponding amine-boranes (2l, 2c, and 2b) in excellent yields in 4 h. Benzylamine-borane (2m) was synthesized in quantitative yield despite the presence of an acidic α-carbon. Acyclic (diethylamine, 1n) as well as cyclic secondary amine (pyrrolidine, 1o) underwent borane protection within 4 h providing 2n and 2o in 96% and 99% yield respectively. Six-membered piperidine (1p) and morpholine (1i) surprisingly took higher reaction times but provided the desired products (2p and 2i respectively) in excellent yields. Both acyclic (1a) and cyclic (1q and 1f) tertiary amines gave the corresponding amine-boranes (2a, 2q and 2f respectively) in slightly lower yields. TEA necessitated the use of 2 equiv. of SBH to achieve optimum yields. N,N'-Dimethylpiperazine-bisborane (2i) was synthesized in 98% yield. Aromatic amine-boranes such as pyridine-borane (2j) and 2-picoline-borane (2k) were produced in near quantitative yields. The lack of nucleophilicity of anilines was exploited to synthesize 2r in quantitative yields. Similarly, N-methylimidazole (1s) underwent *facile* borane protection in 8 h providing 2s in 99% yield.

Scope of Amines:

TABLE 7

Scope of Amines[a]

NaBH$_4$ + NaHCO$_3$ + (H$_{3-n}$)R$_n$N $\xrightarrow[\text{2M THF, rt} \atop \text{4-8 h, -H}_2]{\text{7.2\% v/v H}_2\text{O}}$ (H$_{3-n}$)R$_n$N—BH$_3$ (1.5 equiv) (3 equiv) n = 1,2,3      92-99%[b]

Primary 2l, 4 h, 95%
2c, 4 h, 98%
2b, 4 h, 95%
2m, 4 h, 99%

Secondary 2n, 4 h, 96%
2o, 4 h, 99%
2p, 8 h, 99%
2i, 8 h, 98%

TABLE 7-continued

Scope of Amines[a]

NaBH$_4$ + NaHCO$_3$ + (H$_{3-n}$)R$_n$N $\xrightarrow[\text{2M THF, rt}]{\text{7.2% v/v H}_2\text{O}}$ (H$_{3-n}$)R$_n$N—BH$_3$ (1.5 equiv) (3 equiv) n = 1,2,3  4-8 h, -H$_2$  92-99%[b]

Tertiary 2a, 4 h, 92%[c]

2q, 4 h, 93%

2f, 4 h, 92%

2i, 4 h, 98%

Heteroaromatic 2j, 4 h, 99%

2k, 4 h, 94%

2r, 4 h, 99%

2s, 8 h, 99%[c]

[a]Reactions were performed using 7.5 mmol SBH, 15 mmol of SBC and 5 mmol amine/2.5 mmol diamine in 2M THF at rt, open to air. Water (7.2% v/v of THF) was added dropwise as a 14.4% v/v solution in THF.
[b]Yield of isolated products.
[c]2 equiv. SBH, 4 equiv. SBC, and 4 equiv. water were used.

Figure 1:
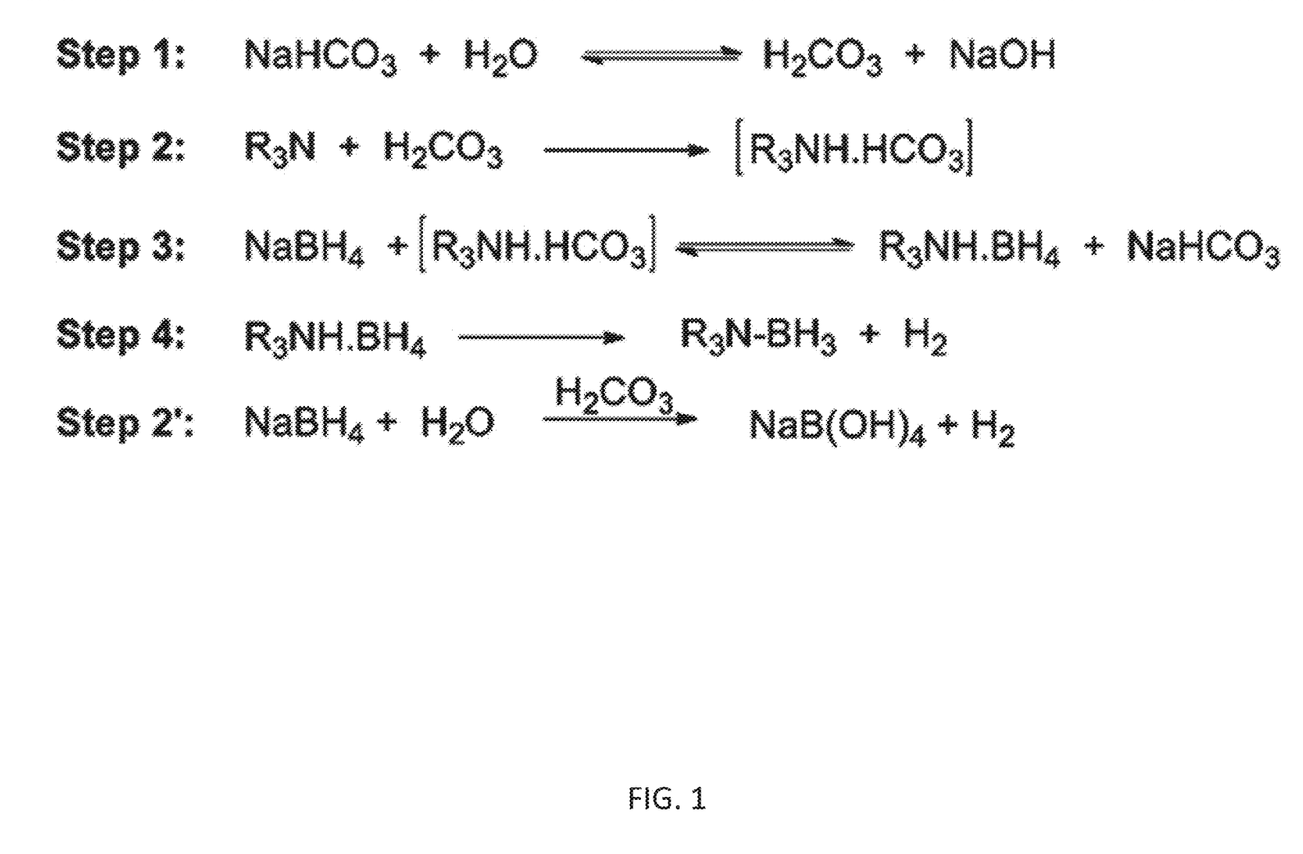
FIG. 1 is a summary of the proposed mechanism for a water-mediated amine-borane synthesis.

The cascade process can be summarized as shown in FIG. 1. Referring to FIG. 1, SBC reacts with water to provide carbonic acid (Step 1). The capture of carbonic acid by amine (Step 2) drives the unfavorable Step 1 reaction equilibrium forward. The alkylammonium bicarbonate salt then undergoes metathesis with sodium borohydride to provide the alkylammonium borohydride salt (Step 3), which due to its inherent instability liberates hydrogen gas to provide the amine-borane (Step 4). The carbonic acid generated in Step 1 can also hydrolyze the sodium borohydride (Step 2') necessitating the use of excess SBH and SBC for complete conversion to amine-boranes.

The above serves to demonstrate a novel water promoted protocol for the near quantitative synthesis of a variety of amine-boranes using sodium borohydride, sodium bicarbonate, and amine in THF. Alkylammonium carbonate is implicated as the plausible reaction intermediate.

Experimental:

$^{11}$B, $^1$H, and $^{13}$C NMR spectra were recorded at room temperature, on a Varian INOVA 300 MHz NMR spectrophotometer. Chemical shifts (δ values) are reported in parts per million relative to BF$_3$.Et$_2$O for $^{11}$B NMR respectively. Data are reported as: δ value, multiplicity (s=singlet, d=doublet, t=triplet, q=quartet, p=pentet, h=hextet, m=multiplet, br=broad) and integration. Tetrahydrofuran (THF, ACS grade containing 0.004% water and 0.025% BHT) was purchased from Fisher-Scientific. Sodium borohydride (SBH, powder, purity >99% by hydride estimation) was purchased in bulk from Dow Chemical Co. (Rohm and Haas). Sodium bicarbonate (ACS reagent, Macron), sodium carbonate (Anhydrous, Macron), sodium bisulfite (Purified, Mallinckrodt), sodium hydrogen sulfate (tech. grade, Sigma-Aldrich), potassium bicarbonate (ACS, Sigma-Aldrich), dipotassium hydrogen phosphate (Anhydrous, Fluka), and potassium dihydrogen phosphate (Assay >99.5%, Fluka) were purchased from the respective commercial sources and powdered prior to use. All of the amines used were purchased from commercial sources. Liquid amines were distilled while solid amines were used without any purification.

General Procedure for the Preparation of Amine-Boranes:

Sodium borohydride (0.28 g, 7.5 mmol) and powdered sodium bicarbonate (1.26 g, 15 mmol) were transferred to a 50 mL dry round bottom flask, charged with a magnetic stir-bar. The corresponding amine (5 mmol) or diamine (2.5 mmol) was charged into the reaction flask followed by addition of reagent-grade tetrahydrofuran (1.9 mL) at rt. Under vigorous stirring, 1.9 mL of 14.4% v/v solution water in THF was added drop-wise. Reaction progress was monitored by $^{11}$B NMR spectroscopy (Note: A drop of anhydrous DMSO is added to the reaction aliquot before running the NMR experiment). Upon completion of the reaction (4-8 h, as determined by $^{11}$B NMR spectroscopy), the reaction contents were filtered through sodium sulfate and celite and the solid residue washed with THF. Removal of the solvent in vacuo from the filtrate yielded the corresponding amine-borane in 92-99% yields.

Experimental Procedures and Characterization of Amine-Boranes:

N,N,N-Triethylamine-Borane (2a):

Sodium borohydride (0.38 g, 10 mmol) and powdered sodium bicarbonate (1.68 g, 20 mmol) were transferred to a 50 mL dry round bottom flask, charged with a magnetic stir-bar. N,N,N-Triethylamine (1a, 0.7 mL, 5 mmol) was charged into the reaction flask followed by addition of reagent-grade tetrahydrofuran (2.5 mL) at rt. Under vigorous stiffing, 2.5 mL of 14.4% v/v solution of water in THF was added drop-wise. Reaction progress was monitored by $^{11}$B NMR spectroscopy (Note: A drop of anhydrous DMSO is added to the reaction aliquot before running the NMR experiment). Upon completion of the reaction (4 h, as determined by $^{11}$B NMR), the reaction contents were filtered through sodium sulfate and celite and the solid residue washed with THF. Removal of the solvent in vacuo from the filtrate yielded 0.53 g (92%) N,N,N-triethylamine-borane (2a) as a colorless liquid.

¹H NMR (300 MHz, CDCl₃) δ (ppm): 2.79 (qd, J=7.4, 1.7 Hz, 6H), 1.19 (td, J=7.3, 1.7 Hz, 9H), 2.10-0.9 (br q, BH₃); ¹³C NMR (75 MHz, CDCl₃) δ (ppm): 52.2, 8.6. ¹¹B NMR (96 MHz, CDCl₃) δ (ppm): −13.95 (q, J=96.0 Hz).

1-Propanamine-Borane (2l):

Sodium borohydride (0.28 g, 7.5 mmol) and powdered sodium bicarbonate (1.26 g, 15 mmol) were transferred to a 50 mL dry round bottom flask, charged with a magnetic stir-bar. 1-Propanamine (1l, 0.41 mL, 5 mmol) was charged into the reaction flask followed by addition of reagent-grade tetrahydrofuran (1.9 mL) at rt. Under vigorous stiffing, 1.9 mL of 14.4% v/v solution water in THF was added drop-wise. Reaction progress was monitored by ¹¹B NMR spectroscopy (Note: A drop of anhydrous DMSO is added to the reaction aliquot before running the NMR experiment). Upon completion of the reaction (4 h, as determined by ¹¹B NMR), the reaction contents were filtered through sodium sulfate and celite and the solid residue washed with THF. Removal of the solvent in vacuo from the filtrate yielded 0.35 g (95%) of 1-propanamine-borane (2l) as a white solid.

¹H NMR (300 MHz, CDCl₃) δ (ppm): 3.83 (s, 2H), 2.78 (p, J=7.3 Hz, 2H), 1.65 (h, J=7.4 Hz, 2H), 0.96 (t, J=7.4 Hz, 3H), 0.75-2.00 (br q, BH₃); ¹³C NMR (75 MHz, CDCl₃) δ (ppm): 50.3, 22.3, 11.0; ¹¹B NMR (96 MHz, CDCl₃) δ (ppm): −19.81 (q, J=96.0 Hz).

Cyclohexylamine-Borane (2c):

Sodium borohydride (0.28 g, 7.5 mmol) and powdered sodium bicarbonate (1.26 g, 15 mmol) were transferred to a 50 mL dry round bottom flask, charged with a magnetic stir-bar. Cyclohexylamine (1c, 0.57 mL, 5 mmol) was charged into the reaction flask followed by addition of reagent-grade tetrahydrofuran (1.9 mL) at rt. Under vigorous stiffing, 1.9 mL of 14.4% v/v solution water in THF was added drop-wise. Reaction progress was monitored by ¹¹B NMR spectroscopy (Note: A drop of anhydrous DMSO is added to the reaction aliquot before running the NMR experiment). Upon completion of the reaction (4 h, as determined by ¹¹B NMR), the reaction contents were filtered through sodium sulfate and celite and the solid residue washed with THF. Removal of the solvent in vacuo from the filtrate yielded 0.55 g (98%) of cyclohexylamine-borane (2c) as a white solid.

¹H NMR (300 MHz, CDCl₃) δ (ppm): 3.59 (s, 2H), 2.72 (tdt, J=10.4, 7.7, 3.0 Hz, 1H), 2.22-2.09 (m, 2H), 1.86-1.57 (m, 3H), 1.42-1.06 (m, 5H), 0.90-2.05 (br q, BH₃); ¹³C NMR (75 MHz, CDCl₃) δ (ppm): 56.8, 32.2, 25.2, 24.4; ¹¹B NMR (96 MHz, CDCl₃) δ (ppm): −20.88 (q, J=95.0 Hz).

Tert-Butylamine-Borane (2b):

Sodium borohydride (0.28 g, 7.5 mmol) and powdered sodium bicarbonate (1.26 g, 15 mmol) were transferred to a 50 mL dry round bottom flask, charged with a magnetic stir-bar. tert-Butylamine (1b, 0.53 mL, 5 mmol) was charged into the reaction flask followed by addition of reagent-grade tetrahydrofuran (1.9 mL) at rt. Under vigorous stiffing, 1.9 mL of 14.4% v/v solution water in THF was added drop-wise. Reaction progress was monitored by ¹¹B NMR spectroscopy (Note: A drop of anhydrous DMSO is added to the reaction aliquot before running the NMR experiment). Upon completion of the reaction (4 h, as determined by ¹¹B NMR), the reaction contents were filtered through sodium sulfate and celite and the solid residue washed with THF. Removal of the solvent in vacuo from the filtrate yielded 0.41 g (98%) of tert-butylamine-borane (2b) as a white solid.

¹H NMR (300 MHz, CDCl₃) δ (ppm): 3.81 (s, 2H), 1.22 (s, 9H), 2.0-0.7 (br q, BH₃); ¹³C NMR (75 MHz, CDCl₃) δ (ppm): 51.9, 26.8; ¹¹B NMR (96 MHz, CDCl₃) δ (ppm): −23.35 (q, J=93.9 Hz).

Benzylamine-Borane (2m):

Sodium borohydride (0.28 g, 7.5 mmol) and powdered sodium bicarbonate (1.26 g, 15 mmol) were transferred to a 50 mL dry round bottom flask, charged with a magnetic stir-bar. Benzylamine (1m, 0.55 mL, 5 mmol) was charged into the reaction flask followed by addition of reagent-grade tetrahydrofuran (1.9 mL) at rt. Under vigorous stiffing, 1.9 mL of 14.4% v/v solution water in THF was added drop-wise. Reaction progress was monitored by ¹¹B NMR spectroscopy (Note: A drop of anhydrous DMSO is added to the reaction aliquot before running the NMR experiment). Upon completion of the reaction (4 h, as determined by ¹¹B NMR), the reaction contents were filtered through sodium sulfate and celite and the solid residue washed with THF. Removal of the solvent in vacuo from the filtrate yielded 0.61 g (99%) of benzylamine-borane (2m) as a white solid.

¹H NMR (300 MHz, DMSO-d₆) δ (ppm): 7.59-7.23 (m, 5H), 5.70 (br, 2H), 3.71-3.46 (m, 2H), 2.28-0.69 (br, BH₃); ¹³C NMR (75 MHz, DMSO-d₆) δ (ppm): 137.0, 128.3, 128.0, 127.2, 51.8; ¹¹B NMR (96 MHz, THF) δ (ppm): −19.02 (q, J=98.7 Hz).

N,N-Diethylamine-Borane (2n):

Sodium borohydride (0.28 g, 7.5 mmol) and powdered sodium bicarbonate (1.26 g, 15 mmol) were transferred to a 50 mL dry round bottom flask, charged with a magnetic stir-bar. N,N-diethylamine (1n, 0.52 mL, 5 mmol) was charged into the reaction flask followed by addition of reagent-grade tetrahydrofuran (1.9 mL) at rt. Under vigorous stiffing, 1.9 mL of 14.4% v/v solution water in THF was added drop-wise. Reaction progress was monitored by ¹¹B NMR spectroscopy (Note: A drop of anhydrous DMSO is added to the reaction aliquot before running the NMR experiment). Upon completion of the reaction (4 h, as determined by ¹¹B NMR), the reaction contents were filtered through sodium sulfate and celite and the solid residue washed with THF. Removal of the solvent in vacuo from the filtrate yielded 0.42 g (96%) of N,N-diethylamine-borane (2n) as a colorless liquid.

¹H NMR (300 MHz, CDCl₃) δ (ppm): 3.42 (s, 1H), 2.98-2.72 (m, 4H), 1.27 (td, J=7.3, 0.9 Hz, 6H), 0.90-2.10 (br q, BH₃); ¹³C NMR (75 MHz, CDCl₃) δ (ppm): 48.8, 11.7; ¹¹B NMR (96 MHz, CDCl₃) δ (ppm): −17.16 (q, J=96.0 Hz).

Pyrrolidine-Borane (2o):

Sodium borohydride (0.28 g, 7.5 mmol) and powdered sodium bicarbonate (1.26 g, 15 mmol) were transferred to a 50 mL dry round bottom flask, charged with a magnetic stir-bar. Pyrrolidine (1o, 0.42 mL, 5 mmol) was charged into the reaction flask followed by addition of reagent-grade tetrahydrofuran (1.9 mL) at rt. Under vigorous stirring, 1.9 mL of 14.4% v/v solution water in THF was added drop-wise. Reaction progress was monitored by ¹¹B NMR spectroscopy (Note: A drop of anhydrous DMSO is added to the reaction aliquot before running the NMR experiment). Upon completion of the reaction (4 h, as determined by ¹¹B NMR), the reaction contents were filtered through sodium sulfate and celite and the solid residue washed with THF. Removal of the solvent in vacuo from the filtrate yielded 0.42 g (99%) of pyrrolidine-borane (2o) as a colorless liquid.

¹H NMR (300 MHz, CDCl₃) δ (ppm): 4.60 (s, 1H), 3.27 (dd, J=10.6, 4.5 Hz, 2H), 2.84-2.58 (m, 2H), 2.06-1.78 (m, 4H), 0.80-2.00 (br q, BH₃); ¹³C NMR (75 MHz, CDCl₃) δ (ppm): 54.4, 24.9; ¹¹B NMR (96 MHz, CDCl₃) δ (ppm): −17.12 (q, J=95.4 Hz).

Piperidine-Borane (2p):

Sodium borohydride (0.28 g, 7.5 mmol) and powdered sodium bicarbonate (1.26 g, 15 mmol) were transferred to a 50 mL dry round bottom flask, charged with a magnetic stir-bar. Piperidine (1p, 0.49 mL, 5 mmol) was charged into the reaction flask followed by addition of reagent-grade tetrahydrofuran (1.9 mL) at rt. Under vigorous stirring, 1.9 mL of 14.4% v/v solution water in THF was added drop-wise. Reaction progress was monitored by $^{11}$B NMR spectroscopy (Note: A drop of anhydrous DMSO is added to the reaction aliquot before running the NMR experiment). Upon completion of the reaction (8 h, as determined by $^{11}$B NMR), the reaction contents were filtered through sodium sulfate and celite and the solid residue washed with THF. Removal of the solvent in vacuo from the filtrate yielded 0.49 g (99%) of piperidine-borane (2p) as a white solid.

$^1$H NMR (300 MHz, CDCl$_3$) δ (ppm): 3.63 (s, 1H), 3.35-3.18 (m, 2H), 2.52 (tdd, J=13.6, 12.4, 11.5, 2.7 Hz, 2H), 1.89-1.72 (m, 3H), 1.65-1.27 (m, 4H), 0.80-2.05 (br q, BH$_3$); $^{13}$C NMR (75 MHz, CDCl$_3$) δ (ppm): 53.2, 25.3, 22.4; $^{11}$B NMR (96 MHz, CDCl$_3$) δ (ppm): −15.49 (q, J=95.0 Hz).

Morpholine-Borane (2i):

Sodium borohydride (0.28 g, 7.5 mmol) and powdered sodium bicarbonate (1.26 g, 15 mmol) were transferred to a 50 mL dry round bottom flask, charged with a magnetic stir-bar. Morpholine (1i, 0.44 mL, 5 mmol) was charged into the reaction flask followed by addition of reagent-grade tetrahydrofuran (1.9 mL) at rt. Under vigorous stirring, 1.9 mL of 14.4% v/v solution water in THF was added drop-wise. Reaction progress was monitored by $^{11}$B NMR spectroscopy (Note: A drop of anhydrous DMSO is added to the reaction aliquot before running the NMR experiment). Upon completion of the reaction (8 h, as determined by $^{11}$B NMR), the reaction contents were filtered through sodium sulfate and celite and the solid residue washed with THF. Removal of the solvent in vacuo from the filtrate yielded 0.49 g (98%) of morpholine-borane (2i) as a white solid.

$^1$H NMR (300 MHz, CDCl$_3$) δ (ppm): 4.36 (s, 1H), 4.05-3.86 (m, 2H), 3.59 (dt, J=12.7, 2.3 Hz, 2H), 3.11 (m, 2H), 2.95-2.70 (m, 2H), 1.69 (br q, 3H, BH$_3$); $^{13}$C NMR (75 MHz, CDCl$_3$) δ (ppm): 65.5, 51.8; $^{11}$B NMR (96 MHz, THF) δ (ppm): −14.77 (q, J=96.0 Hz).

N-Methylpyrrolidine-Borane (2q):

Sodium borohydride (0.28 g, 7.5 mmol) and powdered sodium bicarbonate (1.26 g, 15 mmol) were transferred to a 50 mL dry round bottom flask, charged with a magnetic stir-bar. N-methylpyrrolidine (1q, 0.52 mL, 5 mmol) was charged into the reaction flask followed by addition of reagent-grade tetrahydrofuran (1.9 mL) at rt. Under vigorous stiffing, 1.9 mL of 14.4% v/v solution water in THF was added drop-wise. Reaction progress was monitored by $^{11}$B NMR spectroscopy (Note: A drop of anhydrous DMSO is added to the reaction aliquot before running the NMR experiment). Upon completion of the reaction (4 h, as determined by $^{11}$B NMR), the reaction contents were filtered through sodium sulfate and celite and the solid residue washed with THF. Removal of the solvent in vacuo from the filtrate yielded 0.46 g (93%) of N-methylpyrrolidine-borane (2q) as a colorless liquid.

$^1$H NMR (300 MHz, CDCl$_3$) δ (ppm): 3.21 (tdd, J=7.9, 4.2, 1.7 Hz, 2H), 2.85-2.71 (m, 2H), 2.26-2.10 (m, 2H), 2.02-1.90 (m, 2H), 2.25-1.10 (br q, BH$_3$); $^{13}$C NMR (75 MHz, CDCl$_3$) δ (ppm): 62.7, 51.1, 23.0; $^{11}$B NMR (96 MHz, CDCl$_3$) δ (ppm): −11.03 (q, J=97.0 Hz).

N-Ethylpiperidine-Borane (2f):

Sodium borohydride (0.28 g, 7.5 mmol) and powdered sodium bicarbonate (1.26 g, 15 mmol) were transferred to a 50 mL dry round bottom flask, charged with a magnetic stir-bar. N-Ethylpiperidine (1f, 0.69 mL, 5 mmol) was charged into the reaction flask followed by addition of reagent-grade tetrahydrofuran (1.9 mL) at rt. Under vigorous stiffing, 1.9 mL of 14.4% v/v solution water in THF was added drop-wise. Reaction progress was monitored by $^{11}$B NMR spectroscopy (Note: A drop of anhydrous DMSO is added to the reaction aliquot before running the NMR experiment). Upon completion of the reaction (4 h, as determined by $^{11}$B NMR), the reaction contents were filtered through sodium sulfate and celite and the solid residue washed with THF. Removal of the solvent in vacuo from the filtrate yielded 0.58 g (92%) of N-ethylpiperidine-borane (2f) as a colorless liquid.

$^1$H NMR (300 MHz, CDCl$_3$) δ (ppm): 3.03-2.80 (m, 4H), 2.80-2.67 (m, 2H), 1.94-1.78 (m, 2H), 1.70-1.49 (m, 4H), 1.27 (t, J=7.2 Hz, 3H), 2.10-0.95 (br q, BH$_3$); $^{13}$C NMR (75 MHz, CDCl$_3$) δ (ppm): 57.4, 54.6, 22.7, 20.3, 8.8; $^{11}$B NMR (96 MHz, CDCl$_3$) δ (ppm): −13.01 (q, J=97.0 Hz).

N,N-Dimethylpiperazine-Bisborane (2i):

Sodium borohydride (0.28 g, 7.5 mmol) and powdered sodium bicarbonate (1.26 g, 15 mmol) were transferred to a 50 mL dry round bottom flask, charged with a magnetic stir-bar. N,N-dimethylpiperazine (1i, 0.34 mL, 2.5 mmol) was charged into the reaction flask followed by addition of reagent-grade tetrahydrofuran (1.9 mL) at rt. Under vigorous stirring, 1.9 mL of 14.4% v/v solution water in THF was added drop-wise. Reaction progress was monitored by $^{11}$B NMR spectroscopy (Note: A drop of anhydrous DMSO is added to the reaction aliquot before running the NMR experiment). Upon completion of the reaction (4 h, as determined by $^{11}$B NMR), the reaction contents were filtered through sodium sulfate and celite and the solid residue washed with THF. Removal of the solvent in vacuo from the filtrate yielded 0.35 g (98%) of N,N-dimethylpiperazine-bisborane (2i) as a white solid.

$^1$H NMR (300 MHz, DMSO-d$_6$) δ (ppm): 3.07 (d, J=10.7 Hz, 4H), 2.90 (d, J=11.7 Hz, 4H), 2.58 (s, 6H), 1.30 (br q, 6H, BH$_3$); $^{13}$C NMR (75 MHz, DMSO-d$_6$) δ (ppm): 53.7; $^{11}$B NMR (96 MHz, THF) δ (ppm): −12.29 (q, J=99.8 Hz).

Pyridine-Borane (2j):

Sodium borohydride (0.28 g, 7.5 mmol) and powdered sodium bicarbonate (1.26 g, 15 mmol) were transferred to a 50 mL dry round bottom flask, charged with a magnetic stir-bar. Pyridine (1j, 0.40 mL, 5 mmol) was charged into the reaction flask followed by addition of reagent-grade tetrahydrofuran (1.9 mL) at rt. Under vigorous stiffing, 1.9 mL of 14.4% v/v solution water in THF was added drop-wise. Reaction progress was monitored by $^{11}$B NMR spectroscopy (Note: A drop of anhydrous DMSO is added to the reaction aliquot before running the NMR experiment). Upon completion of the reaction (4 h, as determined by $^{11}$B NMR), the reaction contents were filtered through sodium sulfate and celite and the solid residue washed with THF. Removal of the solvent in vacuo from the filtrate yielded 0.46 g (99%) of pyridine-borane (2j) as a colorless liquid.

$^1$H NMR (300 MHz, CDCl$_3$) δ (ppm): 8.57 (d, J=5.5 Hz, 2H), 7.95 (td, J=7.7, 1.6 Hz, 1H), 7.59-7.48 (m, 2H), 2.62 (q, J=96 Hz, 3H, BH$_3$); $^{13}$C NMR (75 MHz, CDCl$_3$) δ (ppm): 146.8, 138.8, 125.0; $^{11}$B NMR (96 MHz, CDCl$_3$) δ (ppm): −12.57 (q, J=97.7 Hz).

2-Picoline-Borane (2k):

Sodium borohydride (0.28 g, 7.5 mmol) and powdered sodium bicarbonate (1.26 g, 15 mmol) were transferred to a 50 mL dry round bottom flask, charged with a magnetic stir-bar. 2-Picoline (1k, 0.49 mL, 5 mmol) was charged into the reaction flask followed by addition of reagent-grade tetrahydrofuran (1.9 mL) at rt. Under vigorous stirring, 1.9 mL of 14.4% v/v solution water in THF was added drop-wise. Reaction progress was monitored by $^{11}$B NMR spectroscopy (Note: A drop of anhydrous DMSO is added to the reaction aliquot before running the NMR experiment). Upon completion of the reaction (4 h, as determined by $^{11}$B NMR), the reaction contents were filtered through sodium sulfate and celite and the solid residue washed with THF. Removal of the solvent in vacuo from the filtrate yielded 0.50 g (94%) of 2-picoline-borane (2k) as a white solid.

$^{1}$H NMR (300 MHz, CDCl$_3$) δ (ppm): 8.72 (d, J=6 Hz, 1H), 7.89-7.72 (m, 1H), 7.36 (dd, J=7.7, 1.4 Hz, 1H), 7.28 (ddd, J=7.7, 6.1, 1.7 Hz, 1H), 3.10-1.80 (br q, BH$_3$), 2.75 (s, 3H); $^{13}$C NMR (75 MHz, CDCl$_3$) δ 157.2, 148.2, 139.0, 126.3, 122.0, 22.5; $^{11}$B NMR (96 MHz, CDCl$_3$) δ (ppm): −14.22 (q, J=97.9 Hz).

4-Dimethylaminopyridine-Borane (DMAP-BH$_3$, 2r):

Sodium borohydride (0.28 g, 7.5 mmol) and powdered sodium bicarbonate (1.26 g, 15 mmol) were transferred to a 50 mL dry round bottom flask, charged with a magnetic stir-bar. 4-Dimethylaminopyridine (1r, 0.61 g, 5 mmol) was charged into the reaction flask followed by addition of reagent-grade tetrahydrofuran (5.6 mL) at rt. Under vigorous stirring, 1.9 mL of 14.4% v/v solution water in THF was added drop-wise. Reaction progress was monitored by $^{11}$B NMR spectroscopy (Note: A drop of anhydrous DMSO is added to the reaction aliquot before running the NMR experiment). Upon completion of the reaction (4 h, as determined by $^{11}$B NMR), the reaction contents were filtered through sodium sulfate and celite and the solid residue washed with THF. Removal of the solvent in vacuo from the filtrate yielded 0.67 g (99%) of 4-dimethylaminopyridine-borane (2r) as a white solid.

$^{1}$H NMR (300 MHz, CDCl$_3$) δ (ppm): 8.04-7.97 (m, 2H), 6.51-6.46 (m, 2H), 3.01 (s, 6H), 2.31 (br q, BH$_3$); $^{13}$C NMR (75 MHz, CDCl$_3$) δ (ppm): 154.3, 146.3, 106.3, 39.7; $^{11}$B NMR (96 MHz, CDCl$_3$) δ (ppm): −13.74 (q, J=103.3 Hz).

1-Methylimidazole-Borane (2s)

Sodium borohydride (0.38 g, 10 mmol) and powdered sodium bicarbonate (1.68 g, 20 mmol) were transferred to a 50 mL dry round bottom flask, charged with a magnetic stir-bar. 1-Methylimidazole (1s, 0.4 mL, 5 mmol) was charged into the reaction flask followed by addition of reagent-grade tetrahydrofuran (2.5 mL) at rt. Under vigorous stirring, 2.5 mL of 14.4% v/v solution of water in THF was added drop-wise. Reaction progress was monitored by $^{11}$B NMR spectroscopy (Note: A drop of anhydrous DMSO is added to the reaction aliquot before running the NMR experiment). Upon completion of the reaction (8 h, as determined by $^{11}$B NMR), the reaction contents were filtered through sodium sulfate and celite and the solid residue washed with THF. Removal of the solvent in vacuo from the filtrate yielded 0.47 g (99%) 1-methylimidazole-borane (2s) as a colorless liquid.

$^{1}$H NMR (300 MHz, CDCl$_3$) δ (ppm): 7.72 (s, 1H), 6.99-6.91 (m, 2H), 3.76 (s, 3H), 2.90-1.50 (br q, BH$_3$); $^{13}$C NMR (75 MHz, CDCl$_3$) δ (ppm): 136.5, 126.9, 121.0, 34.9. $^{11}$B NMR (96 MHz, CDCl$_3$) δ (ppm): −19.79 (q, J=95 Hz).

Those skilled in the art will recognize that numerous modifications can be made to the specific implementations described above. The implementations should not be limited to the particular limitations described. Other implementations may be possible. In addition, all references cited herein are indicative of the level of skill in the art and are hereby incorporated by reference in their entirety.

REFERENCES

1. For reviews on amine-boranes, see: (a) Staubitz, A.; Robertson, A. P. M.; Sloan, M. E.; Manners, I. Chem. Rev. 2010, 110, 4023; (b) Carboni, B.; Monnier, L. Tetrahedron 1999, 55, 1197.
2. For reviews on phosphine-boranes, see: (a) Ohff, M.; Holz, J.; Quirmbach, M.; Börner, A. Synthesis 1998, 1998, 1391; (b) Brunel, J. M.; Faure, B.; Maffei, M. Coord. Chem. Rev. 1998, 178-180, Part 1, 665.
3. (a) Gay-Lussac, J. L. Mem. Phys. Chim. Soc. D'Arcueil 1809, 2, 211; (b) Besson, A. Comptes Rendus. 890, 110, 516.
4. (a) Brown, H. C.; Schlesinger, H. I.; Cardon, S. Z. J. Am. Chem. Soc. 1942, 64, 325; (b) Cowley, A. H.; Damasco, M. C. J. Am. Chem. Soc. 1971, 93, 6815.
5. Brown, H. C. Organic Syntheses Via Boranes, Wiley, New York, 1975.
6. Baldwin, R. A.; Washburn, R. M. J. Org. Chem. 1961, 26, 3549.
7. Ramachandran, P. V.; Raju, B. C.; Gagare, P. D. Org. Lett. 2012, 14, 6119.
8. Nainan, K. C.; Ryschkewitsch, G. E. Inorg. Chem. 1969, 8, 2671.
9. Budde, W. L.; Hawthorne, M. F. J. Am. Chem. Soc. 1971, 93, 3147.
10. Potter, R. G.; Camaioni, D. M.; Vasiliu, M.; Dixon, D. A. Inorg. Chem. 2010, 49, 10512.
11. Andrews, G. C.; Crawford, T. C. Tetrahedron Lett. 1980, 21, 693.
12. (a) Ramachandran, P. V.; Gagare, P. D.; Sakavuyi, K.; Clark, P. Tetrahedron Lett. 2010, 51, 3167. (b) Matos, K.; Burkhardt, E. R. in Pharmaceutical Process Chemistry, Wiley-VCH Verlag GmbH & Co. KGaA, 2010, pp. 127-143.
13. Yang, X.; Fox, T.; Berke, H. Org. Biomol. Chem. 2012, 10, 852.
14. Hutchins, R. O.; Learn, K.; Nazer, B.; Pytlewski, D.; Pelter, A. Org. Prep. Proced. Int. 1984, 16, 335.
15. Sonnenschein, M. F.; Webb, S. P.; Cieslinski, R. C.; Wendt, B. L. J. Polym. Sci., Polym. Chem. 2007, 45, 989.
16. Fisher, G. B.; Fuller, J. C.; Harrison, J.; Alvarez, S. G.; Burkhardt, E. R.; Goralski, C. T.; Singaram, B. J. Org. Chem. 1994, 59, 6378.
17. Burnham, B. S. Curr. Med. Chem. 2005, 12, 1995.
18. (a) Carre-Burritt, A. E.; Davis, B. L.; Rekken, B. D.; Mack, N.; Semelsberger, T. A. Energy Environ. Sci. 2014, 7, 1653. (b) Muller, K.; Stark, K.; Muller, B.; Arlt, W. Energy Fuels 2012, 26, 3691. (c) Mal, S. S.; Stephens, F. H.; Baker, R. T. Chem. Commun. 2011, 47, 2922. (d) Hamilton, C. W.; Baker, R. T.; Staubitz, A.; Manners, I. Chem. Soc. Rev. 2009, 38, 279. (e) Staubitz, A.; Robertson, A. P. M.; Manners, I. Chem. Rev. 2010, 110, 4079.
19. Ramachandran, P. V.; Kulkarni, A. S.; Pfeil, M. A.; Dennis, J. D.; Willits, J. D.; Heister, S. D.; Son, S. F.; Pourpoint, T. L. Chem. Eur. J. 2014, 20, 16869.
20. Ramachandran, P. V.; Kulkarni, A. S. RSC Adv. 2014, 4, 26207.
21. Ramachandran, P. V.; Gagare, P. D. Inorg. Chem. 2007, 46, 7810.
22. Ramachandran, P. V.; Mistry, H.; Kulkarni, A. S.; Gagare, P. D. Dalton Trans. 2014, 43, 16580.
23. Heldebrant, D. J.; Karkamkar, A.; Linehan, J. C.; Autrey, T. Energy Environ. Sci. 2008, 1, 156.
24. Chen, X.; Bao, X.; Billet, B.; Shore, S. G.; Zhao, J.-C. Chem.-Eur. J. 2012, 18, 11994.
25. (a) Johnson, H. C.; Hooper, T. N.; Weller, A. S. Synthesis and Application of Organoboron Compounds. In Topics in Organometallic Chemistry; Fernandez, E.; Whiting, A., Eds., 2015, vol. 49, pp 153-220. (b) Vance, J. R.; Schafer, A.; Robertson, A. P. M.; Lee, K.; Turner, J.; Whittell, G. R.; Manners, I. J. Am. Chem. Soc. 2014, 136, 3048 and references cited therein.

26. (a) Kalidindi, S. B.; Sanyal, U.; Jagirdar, B. R. *ChemSusChem* 2011, 4, 317. (b) Lidor-Shalev, O.; Zitoun, D. *RSC Adv.* 2014, 4, 63603.
27. Sergueeva, Z. A.; Sergueev, D. S.; Shaw, B. R. *Nucleosides, Nucleotides Nucleic Acids* 2001, 20, 941.
28. Noth, H.; Beyer, H. *Chem. Ber.* 1960, 93, 931.
29. Andres, C.; Delgado, M.; Pedrosa, R. *Synth. Commun.* 1992, 22, 829.
30. Schaeffer, G.; Anderson, E. *J. Am. Chem. Soc.* 1949, 71, 2143.
31. Kikugawa, Y. *Chem. Pharm. Bull.* 1987, 35, 4988.
32. Kampel, V.; Warshawsky, A. *J. Organomet. Chem.* 1994, 469, 15.
33. Kawase, Y.; Yamagishi, T.; Kutsuma, T.; Zhibao, H.; Yamamoto, Y.; Kimura, T.; Nakata, T.; Kataoka, T.; Yokomatsu, T. *Org. Process Res. Dev.* 2012, 16, 495.
34. Salt-base equilibrium has been described in literature: Kar, R. K.; Bera, S. C. *J. Photochem. Photobiol. A: Chem.* 1991, 56, 195.
35. The reaction at 40° C. was attempted with the knowledge of the *facile* synthesis of AB from SBH and $(NH_4)_2SO_4$ at this temperature.
36. Pfeil, M. A.; Dennis, J. D.; Son, S. F.; Heister, S. D.; Pourpoint, T. L.; Ramachandran, P. V. *J. Propul. Power* 2015, 31, 365.
37. Wideman T.; Sneddon L. G. *Inorg. Chem.* 1995, 34, 1002.
38. Supporting Information: DOI: 10.1021/acs.inorgchem.5b00572.
39. Metal borohydrides are known to hydrolyze in aqueous solutions of sodium bicarbonate. Grice, K. A.; Groenenboom, M. C.; Manuel, J. D. A.; Sovereign, M. A.; Keith, J. A. *Fuel* 2015, 150, 139.

The invention claimed is:

1. A method for preparing amine-boranes, comprising:
reacting a stoichiometric amount of sodium borohydride with a stoichiometric amount of ammonium salt in refluxing THF in the presence of at least one corresponding amine.

2. A method for preparing amine-boranes, comprising:
adding a solution of THF containing about a slight excess than stoichiometric amount of water to a mixture, wherein the mixture comprises:
   a slight excess than stoichiometric amount of sodium borohydride;
   a corresponding amine; and
   a slight excess than stoichiometric amount of sodium bicarbonate.

3. The method of claim 2, wherein the reaction is conducted at room temperature.

4. The method of claim 2, wherein the ratio of amine:sodium borohydride:sodium bicarbonate:water is 1:1.5:3:3.

* * * * *